United States Patent

Mori et al.

[11] Patent Number: 5,886,010
[45] Date of Patent: Mar. 23, 1999

[54] TNF-α INHIBITOR

[75] Inventors: Toyoki Mori, Naruto; Michiaki Tominaga; Yukihisa Ono, both of Itano-gun, all of Japan

[73] Assignee: Otsuka Pharmaceutical Company, Limited, Tokyo, Japan

[21] Appl. No.: 875,056

[22] PCT Filed: Dec. 18, 1995

[86] PCT No.: PCT/JP95/02592

§ 371 Date: Jul. 3, 1997

§ 102(e) Date: Jul. 3, 1997

[87] PCT Pub. No.: WO96/21447

PCT Pub. Date: Jul. 18, 1996

[30] Foreign Application Priority Data

Jan. 9, 1995 [JP] Japan .................................. 7-000932

[51] Int. Cl.⁶ .................................. A61K 31/47
[52] U.S. Cl. .................................. 514/312
[58] Field of Search .................................. 514/312

[56] References Cited

U.S. PATENT DOCUMENTS 5,053,514 10/1991 Fujioka et al. ................ 514/312
5,401,754 3/1995 Fujioka et al. ................ 514/312

*Primary Examiner*—Jerome D. Goldberg
*Attorney, Agent, or Firm*—Sughrue, Mion, Zinn, Macpeak & Seas, PLLC

[57] ABSTRACT

A method for the prophylaxis and treatment of diseases induced by accelerated INF-α secretion, such as rheumatoid arthritis, endotoxin shock, adult respiratory distress syndrome, thermal burn, asthma, myocardial infarction, acute phase of viral myocardiosis, etc. which comprises administering a carbostyril compound of the formula:

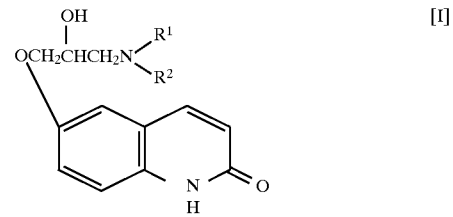

wherein $R^1$ is H or lower alkyl, and $R^2$ is phenyl(lower)alkyl having optionally 1 to 3 lower alkoxy substituents on the phenyl ring, or a pharmaceutically acceptable salt thereof to a subject.

3 Claims, No Drawings

TNF-α INHIBITOR

FIELD OF THE INVENTION

This invention relates to an inhibitor of production or secretion of tumor necrosis factor-α (TNF-α), which comprises as an active ingredient a carbostyril compound or a pharmaceutically acceptable salt thereof.

BACKGROUND OF THE INVENTION

There have been found various cytokines which are a protein inhibiting manifectation of biofunctions such as immunoresponse, inflammatory reaction and hemopoietic function in biobody, and the structures and activities thereof have gradually been clarified. With such clarification, it has also been made clear that they are effective not only onto the immune system but also onto various biofunctions and have much relevance to generation of biobody, differentiation, homeostasis, and pathological physiology.

Among the cytokines, TNF has been found as an antitumor cytokine and has been expected to be useful as an antitumor agent. However, later on it was found that it is identical with cachectin which is a cachexy-inducing factor. It is reported that TNF has an activity of stimulating production of other cytokines such as IL-1, etc., proliferative activity of fibroblast, endotoxin shock-inducing activity, an activity of promoting the adhesion of leukocytes to endothelium by increasing intercellular adhesion molecules (ICAM-1, ICAM-2) or endothelial leukocyte adhesion molecule-i (ELAM-1), an activity of bone absorption, and an activity of inducing arthritis (e.g. cartilage decomposing activity) [cf. Beutler, B., et al., Nature, 316, 552–554 (1985); Peetre, C., et al., J. Clin. Invest., 78, 1694–1700 (1986); Kurt-Jones, E. A., et al., J. Immunol., 139, 2317–2324 (1987); Bevilacqua, M. P., et al., Science, 241, 1160–1165 (1989); Akatu, K. & Suda, T., Medical Practice, 8 (9), 1393–1396 (1991)].

Moreover, it is reported that in bacterial or parasitic infectious diseases, TNF is contained in a higher concentration in blood and cerebrospinal fluid [cf. Mituyama, M., IGAKU-NO-AYUMI, 159 (8), 467–470 (1991); and Nakao, M., IGAKU-NO-AYUMI, 159 (8), 471–474 (1991)]. It is also reported that in rheumatoid arthritis, the joint fluid and blood serum have TNF-α activity [cf. Saxne, T., et al., Arthritis Rheum., 31, 1041 (1988); Chu, C. Q., et al., Arthritis Rheum., 34, 1125–1132 (1991); Macnaul, K. L., et al., J. Immunol., 145, 4154–4166 (1990); Brennan, F. M., et al., J. Immunol., 22, 1907–1912 (1992); and Brennan, F. M., et al., Bri. J. Rheum., 31, 293–298 (1992)].

It is further reported that in patients suffered from a severe respiratory diseases: adult respiratory distress syndrome (ARDS), the phlegm of the patients contain an increased TNF [cf. Millar, A. B., et al., Nature, 324, 73 (1986)], and that TNF participates also in the severity of virus hepatitis [cf. Muto, Y. et al., Lancet, ii, 72–74 (1986)].

It is also reported that the blood concentration of TNF-α raises in case of myocardial ischemia (e.g. acute myocardial infarction) [cf. Latini, R., et al., J. Cardiovasc. Pharmacol., 23, 1–6 (1994)], and it is suggested that TNF-α will participate in such diseases [cf. Lefer, A. M., et al, Science, 249, 61–64 (1990)]. It is recently reported that TNF-α inhibits myocardial contraction [cf. Finkel, M. S., et al., Science, 257, 387–389 (1992); and Pagani, D. F., et al., J. Clin. Invest., 90, 389–398 (1992)].

However, there have never been developed a chemotherapeutic drug which exhibits satisfactory effects on the above-mentioned various diseases such as rheumatoid arthritis, endotoxin shock, or ARDS, and there have merely been used some steroids, antiinflammatory agents, platelet agglutination inhibitors, antibiotics from the nostropic viewpoint. Since it has been suggested the correlation between these diseases and the raising of concentration and activity of TNF-α, it has recently been tried to employ an antibody of TNF-α in the treatment of these diseases, but it did not give satisfactory result. Thus, it has been desired to find and develop a new type drug for the treatment of these diseases by a new mechanism to inhibit the accelerated production or secretion of TNF-α.

By the way, the carbostyril compounds of the formula [I] as shown hereinafter are disclosed in U.S. Pat. No. 5,053,514 as a cardiotonic agent, wherein the processes for the preparation thereof are also disclosed. It is also known that these compounds have myocardial contract increasing activity (i.e. positive inotropic activity), coronary blood flow increasing activity, hypotensive activity, an activity of inhibiting blood vessel contract induced by norepinephrine, and antiinflammatory activity (cf. the above U.S. Patent as well as U.S. Pat. Nos. 5,266,577 and 5,385,914), and are useful as a thrombosis treating agent, phosphodiesterase inhibitor, cerebral circulatory improving agent (cf. U.S. Pat. No. 5,401,754), as an antiarrhythmic agent (cf. WO 94/06427), and as an anti-histaminic agent (cf. Japanese Patent First Publication (Kokai) No. 56-8319). It is also reported that a compound inclusive in the carbostyril compounds of the formula [I]: i.e. 6-[3-(3,4-dimethoxybenzyl)amino-2-hydroxypropoxy]carbostyril has hemodynamic effects in patients with advanced heart failure (cf. Journal of Cardiac Failure, Vol. 1 No. 1 pp. 57–62, Oct. 1994). However, these literatures do not teach or even suggest that the carbostyril compounds have the activities of inhibiting production or secretion of TNF-α.

DISCLOSURE OF THE INVENTION

The present inventors have studied to develop a new TNF-α inhibitor having the desired activities and being suitable for the treatment of the above-mentioned diseases and have found that the carbostyril compounds of the formula [I] as shown below, particularly 6-[3-(3,4-dimethoxybenzyl)amino-2-hydroxypropoxy]carbostyril or a pharmaceutically acceptable salt thereof are useful as a TNF-α inhibitor.

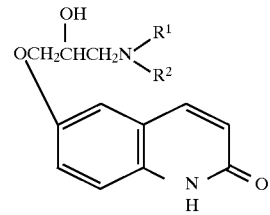

[I]

wherein $R^1$ is hydrogen atom or a lower alkyl, and $R^2$ is a phenyl(lower)alkyl group having optionally 1 to 3 lower alkoxy substituents on the phenyl ring.

An object of the invention is to provide a novel TNF-α inhibitor. Another object of the invention is to provide a new use of the known carbostyril compounds of the formula (I) and their pharmaceutically acceptable salts as a TNF-α inhibitor. A further object is to provide a method for the prophylaxis and treatment of various diseases induced by accelerated production or secretion of TNF-α by administering an effective amount of the carbostyril compounds (I) or a pharmaceutically acceptable salt thereof to the subject suffering from such diseases in human being and other animals.

The TNF-α inhibitor of the present invention is used for the prophylaxis and treatment of various diseases accompanied by the accelerated production or secretion of TNF-α, particularly rheumatoid arthritis, endotoxin shock, adult respiratory distress syndrome (ARDS), thermal burn, asthma, myocardial infarction which is a syndrome of myocardial ischemia, the acute phase of viral myocardiosis, idiopathic dilated cardiomyopathy. It is also used in the coronary artery bypass grafting (CABG) and in the use of artificial heart or lung.

The each group in the formula (I) denotes as follows.

The "lower alkyl group" denotes a straight chain or branched chain alkyl group having 1 to 6 carbon atoms, such as methyl, ethyl, propyl, isopropyl, butyl, tert-butyl, pentyl, hexyl, and the like.

The "lower alkoxy group" denotes a straight chain or branched chain alkoxy group having 1 to 6 carbon atoms, such as methoxy, ethoxy, propoxy, isopropoxy, butoxy, tert-butoxy, pentyloxy, hexyloxy, and the like.

The "phenyl(lower)alkyl group having optionally 1 to 3 lower alkoxy substituents on the phenyl ring" denotes a phenylalkyl group wherein the alkyl moiety is a straight chain or branched chain alkyl group having 1 to 6 carbon atoms and it has 1 to 3 substituents of a straight chain or branched chain alkoxy group having 1 to 6 carbon atoms on the phenyl ring, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl, and the like.

The compounds of the present invention include the compounds of the formula [I] wherein $R^1$ is hydrogen atom and $R^2$ is a phenyl(lower)alkyl group having optionally 1 to 3 lower alkoxy substituents on the phenyl ring, and the compounds of the formula [I] wherein $R^1$ is a lower alkyl group and $R^2$ is a phenyl(lower)alkyl group having optionally 1 to 3 lower alkoxy substituents on the phenyl ring.

Among the carbostyril compounds of the formula (I), basic compounds can easily form a salt with conventional pharmaceutically acceptable acids. These acids include, for example, inorganic acids such as sulfuric acid, nitric acid, hydrochloric acid, phosphoric acid, hydrobromic acid, etc., and organic acids such as acetic acid, p-toluenesulfonic acid, ethanesulfonic acid, oxalic acid, maleic acid, fumaric acid, malic acid, tartaric acid, citric acid, succinic acid, benzolic acid, etc. Besides, among the carbostyril compounds of the formula (I), acidic compounds can easily form a salt with conventional pharmaceutically acceptable basic compounds. These basic compounds include, for example, metal hydroxides such as sodium hydroxide, potassium hydroxide, calcium hydroxide, etc., alkali metal carbonates or hydrogen carbonates such as sodium carbonate, potassium hydrogen carbonate, sodium hydrogen carbonate, etc. The compounds of the present invention include also their optical isomers.

The compounds of the formula (I) and their salts of this invention are used in the form of a conventional pharmaceutical preparation in human being and other animals. The preparation is prepared by using conventional diluents or carriers such as fillers, thickening agents, binders, wetting gents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, emulsion, suspensions, etc.), and the like. In order to form in tablets, there are used conventional carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinyl-pyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets.

In the preparation of pills, the carriers include any conventional carriers, for example, vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include any conventional carriers, for example, polyethylene glycol, cacao butter, higher alcohols, higher alcohol esters, gelatin, semi-synthetic glycerides, and the like.

Capsules can be prepared by charging a mixture of the compound of this invention with the above carriers into hard gelatin capsules or soft capsules in a usual manner.

In the preparation of injections, the solutions, emulsions or suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweetening agents, and other medicaments, if desired.

The amount of the active compound to be incorporated into the pharmaceutical composition of this invention is not specified but may be selected from a broad range, but it is usually in the range of 1 to 70% by weight, preferably about 1 to 30% by weight based on the weight of the composition.

The pharmacetuical composition of this invention may be administered in any method, and suitable method for administration may be determined in accordance with various forms of preparation, ages, sexes and other conditions of the patients, the degree of severity of diseases, and the like. For example, tablets, pills, solutions, suspensions, emulsion, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if desired. Suppositories are administered in intrarectal route.

The dosage of the pharmaceutical composition of this invention may be selected in accordance with the usage, ages, sexes and other conditions of the patients, the degree of severity of the diseases, and the like, but is usually in the range of about 0.1 to 10 mg of the active compound of this invention per 1 kg of body weight of the patient per day. The daily dosage may be administered dividedly in one to four times in a day. The active compound is preferably contained in an amount of about 1 to about 200 mg per the dosage unit.

BEST MODE FOR CARRYING OUT THE INVENTION

The present invention is illustrated by the following pharmacological experiments and preparations.

Pharmacological Experiment

By using 6-[3-(3,4-dimethoxybenzyl)amino-2-hydroxypropoxy]carbostyril (hereinafter, referred to as "Compound 1") as a test compound, the following experiment was done.

A 10% heparinized peripheral blood from healthy volunteer, a test compound (30 μg/ml) and lipopolysaccharide (LPS, 3.3 μg/ml) were added to RPMI-1640 medium (supplemented with penicillin 100 units/ml and streptomycin 0.1 μg/ml), and the mixture was incubated in a 5% $CO_2$ atmosphere at 37° C. for 18–24 hours. The supernatant of the culture was collected by centrifugation. This supernatant was used as a test sample.

The TNF-α was measured by an enzyme immunoassay (EIA) method. The amount of TNF-α in the test sample was determined based upon the standard curve. The detection limit was 20 pg/ml. The results are shown in the following table.

|  | Concentration of TNF-α (pg/ml) |
|---|---|
| Group without addition of test compound | 1211 |
| Group added with Test Compound 1 | 472 |

PREPARATION 1

Tablets are prepared from the following components.

| Components | Amount |
|---|---|
| 6-[3-(3,4-Dimethoxybenzyl)amino-2-hydroxypropoxy]carbostyril | 5 mg |
| Starch | 132 mg |
| Magnesium stearate | 18 mg |
| Lactose | 45 mg |
| Totally | 200 mg |

According to a conventional method, there are prepared tablets which contain the above components in the above-mentioned amounts in each tablet.

PREPARATION 2

Injections are prepared from the following components.

| Components | Amount |
|---|---|
| 6-[3-(3,4-Dimethoxybenzyl)amino-2-hydroxypropoxy]carbostyril | 500 mg |
| Polyethylene glycol (molecular weight: 4000) | 0.3 g |
| Sodium chloride | 0.9 g |
| Polyoxyethylene sorbitane monooleate | 0.4 g |
| Sodium metabisulfite | 0.1 g |
| Methylparaben | 0.18 g |
| Propylparaben | 0.02 g |
| Distilled water for injecton | 100 ml |

The above parabens, sodium metabisulfite and sodium chloride are dissoved in the above distilled water with stirring at 80° C., The resulting solution is cooled to 40° C., and therein are dissolved succesively the active compound of this invention, polyethylene glycol and polyoxyethylene sorbitan monooleate, and thereto is added the distilled water for injection so as to adjust the final volume. The solution is sterilized by filtration with a filter paper and each 1 ml of the solution is poured into an ampoule to give the desired injection.

INDUSTRIAL APPLICATION

The INF-α inhibitor of this invention is useful for the prophylaxis and treatment of various diseases induced by accelerated production or secretion of TNF-α, such as rheumatoid arthritis, endotoxin shock, adult respiratory distress syndrome, thermal burn, asthma, and further myocardial infarction, acute phase of viral myocardiosis, etc.

We claim:

1. A method for the treatment of diseases induced by accelerated TNF-α secretion which comprises administering a therapeutically effective amount of a carbostyril compound of the formula (I):

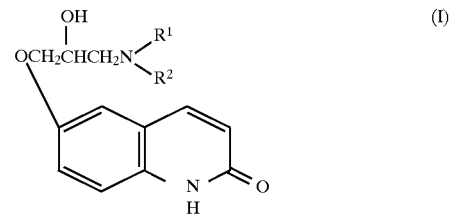

wherein $R^1$ is hydrogen atom or a lower alkyl group, and $R^2$ is a phenyl(lower)alkyl group having optionally 1 to 3 lower alkoxy substituents on the phenyl ring, or a pharmaceutically acceptable salt thereof to a subject; wherein the disease induced by accelerated TNF-α secrection is rheumatoid arthritis, endotoxin shock, adult respiratory distress syndrome, or thermal burn.

2. A method for the treatment of diseases induced by accelerated TNF-α secretion which comprises administering a therapeutically effective amount of a carbostyril compound of the formula (I):

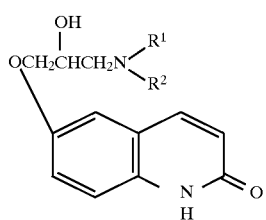

(I)

wherein R¹ is hydrogen atom or a lower alkyl group, and R² is a phenyl(lower)alkyl group having optionally 1 to 3 lower alkoxy substituents on the phenyl ring, or a pharmaceutically acceptable salt thereof to a subject; wherein the disease induced by accelerated TNF-α secrection is a disease selected from myocardial infarction or acute phase of viral myocardiosis.

3. The method according to claim 1 or 2, wherein the active ingredient is 6-[3-(3,4-dimethoxybenzyl)amino-2-hydroxypropoxy]carbostyril or a pharmaceutically acceptable salt thereof.

* * * * *